US006733481B2

(12) United States Patent
Ow

(10) Patent No.: US 6,733,481 B2
(45) Date of Patent: May 11, 2004

(54) CONTAINMENT SYSTEM FOR BIOHAZARDOUS FLUIDS

(75) Inventor: Melody Ow, 892 Filbert St., San Francisco, CA (US) 94133

(73) Assignee: Melody Ow, San Francisco, CA (US)

( * ) Notice: Subject to any disclaimer, the term of this patent is extended or adjusted under 35 U.S.C. 154(b) by 0 days.

(21) Appl. No.: 09/883,095

(22) Filed: Jun. 15, 2001

(65) Prior Publication Data

US 2002/0189706 A1 Dec. 19, 2002

(51) Int. Cl.[7] .................... A61M 1/00; B65B 31/00
(52) U.S. Cl. .................. 604/317; 604/319; 141/59; 141/7
(58) Field of Search ................ 604/317, 319, 604/321, 322, 323, 324, 332, 333; 141/59, 7, 314, 114, 313; 222/490

(56) References Cited

U.S. PATENT DOCUMENTS

| | | | | |
|---|---|---|---|---|
| 3,032,037 A | * | 5/1962 | Huber ................. 604/245 |
| 3,312,221 A | * | 4/1967 | Overment ........... 128/DIG. 24 |
| 3,364,941 A | * | 1/1968 | Harder ................. 137/849 |
| 3,439,677 A | * | 4/1969 | Bonfils ................. 604/333 |
| 3,463,159 A | * | 8/1969 | Heimlich ............... 604/247 |
| 3,478,922 A | * | 11/1969 | Mole ................... 220/86.2 |
| 3,529,599 A | * | 9/1970 | Folkman ............... 604/323 |
| 3,537,456 A | * | 11/1970 | Harautuneian .......... 222/527 |
| 3,575,170 A | * | 4/1971 | Clark ................. 261/101 |
| 3,602,223 A | * | 8/1971 | Engelsher ............. 604/138 |
| 3,680,560 A | * | 8/1972 | Pannier et al. ......... 604/320 |
| 3,731,684 A | * | 5/1973 | Spiegel ................ 285/319 |
| 3,739,936 A | * | 6/1973 | Jones, Jr. ............ 220/86.1 |
| 3,800,795 A | * | 4/1974 | Walker ............... 604/138 |
| 3,845,765 A | * | 11/1974 | Ikeda ................. 604/319 |
| 3,937,395 A | | 2/1976 | Lawes ................. 229/62.5 |
| 3,998,255 A | * | 12/1976 | Mather et al. .......... 383/102 |
| 4,017,020 A | | 4/1977 | Frank ................. 229/62 |
| 4,111,204 A | * | 9/1978 | Hessel ................ 604/321 |
| 4,113,149 A | | 9/1978 | Harsch ................ 222/181 |
| 4,254,771 A | * | 3/1981 | Vidal ............... 128/DIG. 24 |
| 4,289,166 A | * | 9/1981 | Haines ................. 137/846 |
| 4,295,244 A | | 10/1981 | Herpers et al. .......... 15/320 |
| 4,306,557 A | | 12/1981 | North ................. 128/276 |
| 4,314,558 A | | 2/1982 | Korpman ............... 128/283 |
| 4,356,012 A | * | 10/1982 | Hofstetter ............. 156/290 |
| 4,392,858 A | * | 7/1983 | George et al. .......... 604/133 |
| 4,427,425 A | * | 1/1984 | Briggs et al. .......... 604/333 |
| 4,441,209 A | | 4/1984 | Lunshof et al. ......... 383/45 |
| 4,455,140 A | | 6/1984 | Joslin ................. 604/317 |
| 4,461,402 A | | 7/1984 | Fell et al. ............ 222/105 |
| 4,496,354 A | * | 1/1985 | Steer et al. .......... 206/466 |
| 4,509,642 A | | 4/1985 | Rowell ................. 206/219 |
| 4,516,973 A | * | 5/1985 | Telang ................. 604/319 |
| 4,545,497 A | * | 10/1985 | Martha, Jr. ............ 215/253 |
| 4,635,814 A | | 1/1987 | Jones ................. 220/403 |
| 4,713,859 A | | 12/1987 | Smith, Jr. ............ 15/264 |

(List continued on next page.)

FOREIGN PATENT DOCUMENTS

GB     2084879 A   *   4/1982

*Primary Examiner*—Gregory L. Huson
*Assistant Examiner*—Khoa Huynh
(74) *Attorney, Agent, or Firm*—Wilson Sonsini Goodrich & Rosati

(57) ABSTRACT

A containment system for biohazardous fluids is described. The containment system operates under the action of gravity at substantially constant atmospheric pressure. The system includes a container having a first membrane and a second membrane coupled together to enclose a containment volume. The first membrane is characterized by being permeable to gases and impermeable to liquids and aerosols. The second membrane is characterized by being impermeable to gasses and liquids and includes an inlet port configured to receive a tube. A self-sealing inlet port minimizes splashing back and spillage. Particular embodiments include a single-use liner assembly and a rigid, reusable receptacle with a securable lid and a drain for disposing of collected fluids. The receptacle may be coupled to the liner assembly to substantially enclose the liner.

32 Claims, 4 Drawing Sheets

U.S. PATENT DOCUMENTS

| | | | | |
|---|---|---|---|---|
| 4,723,944 A | * | 2/1988 | Jensen | 604/323 |
| 4,724,682 A | | 2/1988 | Flum et al. | 62/462 |
| 4,798,307 A | | 1/1989 | Evrard | 220/20.5 |
| 4,809,679 A | * | 3/1989 | Shimonaka et al. | 600/154 |
| 4,809,860 A | | 3/1989 | Allen | 220/20.5 |
| 4,863,446 A | | 9/1989 | Parker | 604/317 |
| 4,957,492 A | * | 9/1990 | McVay | 600/573 |
| 4,995,238 A | | 2/1991 | King | 62/125 |
| 5,025,947 A | * | 6/1991 | Leone | 220/229 |
| 5,092,378 A | | 3/1992 | Dunham | 141/237 |
| 5,119,675 A | * | 6/1992 | Mohiuddin | 600/580 |
| 5,143,242 A | | 9/1992 | Millasich | 220/404 |
| 5,147,065 A | * | 9/1992 | Rush et al. | 215/229 |
| 5,202,093 A | * | 4/1993 | Cloyd | 215/247 |
| 5,230,566 A | | 7/1993 | Jackson et al. | 383/66 |
| 5,257,423 A | | 11/1993 | Jacobsen et al. | 4/630 |
| 5,409,014 A | * | 4/1995 | Napoli et al. | 600/575 |
| 5,647,414 A | | 7/1997 | Brittain et al. | 141/231 |
| 5,688,255 A | | 11/1997 | Hand | 604/317 |
| 5,755,057 A | | 5/1998 | Dancer | 43/54.1 |
| 5,792,126 A | | 8/1998 | Tribastone et al. | 604/319 |
| 5,881,901 A | | 3/1999 | Hampton | 220/495.08 |
| 5,884,810 A | | 3/1999 | Vizcarra et al. | 222/83 |
| 5,914,047 A | | 6/1999 | Griffiths | 210/739 |
| 5,934,345 A | | 8/1999 | Moynihan et al. | 141/313 |
| 5,950,251 A | | 9/1999 | Cost et al. | 4/483 |
| 5,971,194 A | | 10/1999 | Freedland | 220/495.08 |
| 5,987,708 A | | 11/1999 | Newton | 24/30.5 |
| 6,003,717 A | | 12/1999 | Long | 220/495.11 |
| 6,029,844 A | | 2/2000 | Brady | 220/495.08 |
| 6,042,850 A | | 3/2000 | Ida et al. | 426/2 |
| 6,050,432 A | | 4/2000 | Kochnke | 215/11.3 |
| 6,093,230 A | * | 7/2000 | Johnson et al. | 55/482 |
| 2001/0042572 A1 | * | 11/2001 | Faughey et al. | |

* cited by examiner

TOP VIEW

CONTAINMENT SYSTEM FOR BIOHAZARDOUS FLUIDS

INTRODUCTION

Bodily fluids, at one time considered to pose no significant hazards, are now understood to be biohazardous. The hazards extend to care providers as well as patients since the fluids can transfer pathogenic compounds such as viruses and bacteria. In response to this heightened awareness of risk, mitigation of such biohazards is becoming a standard of care in the medical profession.

Mitigation schemes depend on the mode or manner of possible exposure. In the context of medical surgery, for example, the exposure may occur from contact with a patient's undiluted bodily fluids or from contact with bodily fluids diluted in irrigation liquids that are used during surgery. The fluids are typically in macroscopic form. However, exposure may also occur from contact with small aerosols containing bodily fluids. Aerosols may be generated during the surgery by, for example, the action of surgical tools. Other seemingly risk-free actions, such as pouring liquid waste into drains during or after surgery, may also produce aerosols. Once an aerosol is generated, small droplets of fluid migrate throughout the surgery environment and pose a distributed hazard.

The most advanced surgery facilities may be well equipped to mitigate many modes of exposure to biohazardous fluids. However, many environments in which surgery is performed are not well equipped. In fact, many surgeries are performed in an environment that is more like an office than a hospital. For example, arthroscopic surgery on the shoulder or knee is commonly performed outside of a hospital in a medical practitioner's office. During such a surgery, irrigation fluid is infused into the joint by a gravity-feed system. A resulting mixture of irrigation fluid and the patient's bodily fluids is commonly drained from the surgery site and collected in an open bucket or receptacle placed on the floor. Eventually, the contents of the receptacle are poured into a sewer drain.

Such common practices can and should be improved according to a higher standard of care that includes mitigation of biohazard exposure modes. However, prior art containment systems that might be used are not simple and economical since they typically include expensive, bulky vacuum pumps and other hardware. Thus, many medical practitioners continue procedures that expose both patients and care providers to biohazards. To transition to a higher standard of care, simple, economical, closed containment systems for biohazardous fluids are needed. Such systems are complementary alternatives to more elaborate and expensive prior art devices in the marketplace.

SUMMARY

This invention is a containment system for biohazardous fluids. In an embodiment, the containment system includes a container having a first membrane and a second membrane coupled together to enclose a containment volume. The first membrane has a characteristic property of being permeable to gases and impermeable to liquids and aerosols. Differing embodiments have a first membrane impermeable to objects having a size greater than 10 micrometers, or 1 micrometer, or 0.1 micrometer. Suitable materials for the first membrane include polymers such as polytetrafluoroethylene (PTFE).

The second membrane has a characteristic property of being impermeable to gasses and liquids and includes an inlet port configured to receive a tube. In certain embodiments, the second membrane may be transparent to visible light. The inlet port may have several membranes that self-seal about the surface of a member piercing through the elastic membrane. In other embodiments, the inlet port includes a diaphragm, which may be fabricated from a silastic material. The diaphragm may be formed from a plurality of leaves, or overlapping semi-circular disk portions.

Other embodiments include a single-use liner assembly and a rigid, reusable receptacle coupled to and substantially enclosing the liner assembly. The single-use liner assembly includes a biohazard container. In certain embodiments, the second membrane of the container may have an outlet port and the liner assembly may include an elastic band. Both the reusable receptacle and the liner assembly may be transparent to visible light. Further embodiments include a lid that is securable to the reusable receptacle to completely enclose the liner assembly.

DETAILED DESCRIPTION

Figure 1:
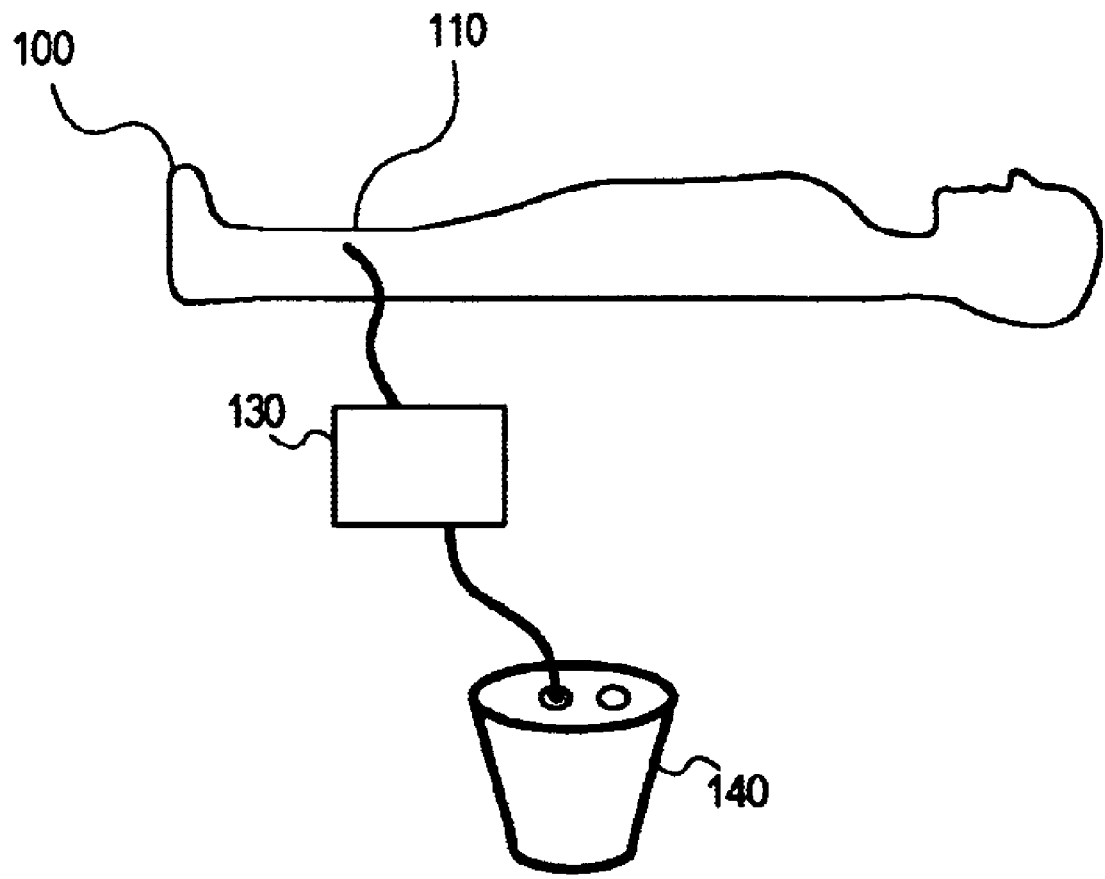
FIG. 1 illustrates an embodiment used in the context of surgery.

FIG. 1 illustrates an embodiment of a containment system for biohazardous fluids used in the context of surgery. In FIG. 1, patient 100, surgery site 110, fluid collection apparatus 130 and containment system 140 are shown. The collection apparatus collects fluid from the surgery site and may comprise a simple funnel and tubing or a more complicated apparatus. Many variations are well understood in the medical profession. The collected fluid includes bodily fluids from the patient and may also include substantial proportions of irrigation fluid introduced into the surgical site by medical personnel to aid in the surgery procedures.

According to the embodiment shown in FIG. 1, the collected fluid from surgery site 110 is transferred to a closed containment system 140. In contrast to prior art systems where a motive force for fluid flow is provided by a vacuum-induced pressure (a surface force) gradient, the embodiment shown operates at substantially constant atmospheric pressure and relies on gravity (a body force) to induce fluid flow. Accordingly, the containment system is located below the surgery site in a preferred manner of use.

A containment system operating with a substantially constant gas pressure (typically atmospheric pressure) affords greatly improved simplicity and cost and is sufficient for many applications. However, to operate at atmospheric pressure while receiving fluid, a difficulty must be overcome. Biohazards, including those possibly transferred from the contained fluids into the air within the containment system, must remain within the system while allowing air displaced by the entering fluid to escape.

Figure 2:
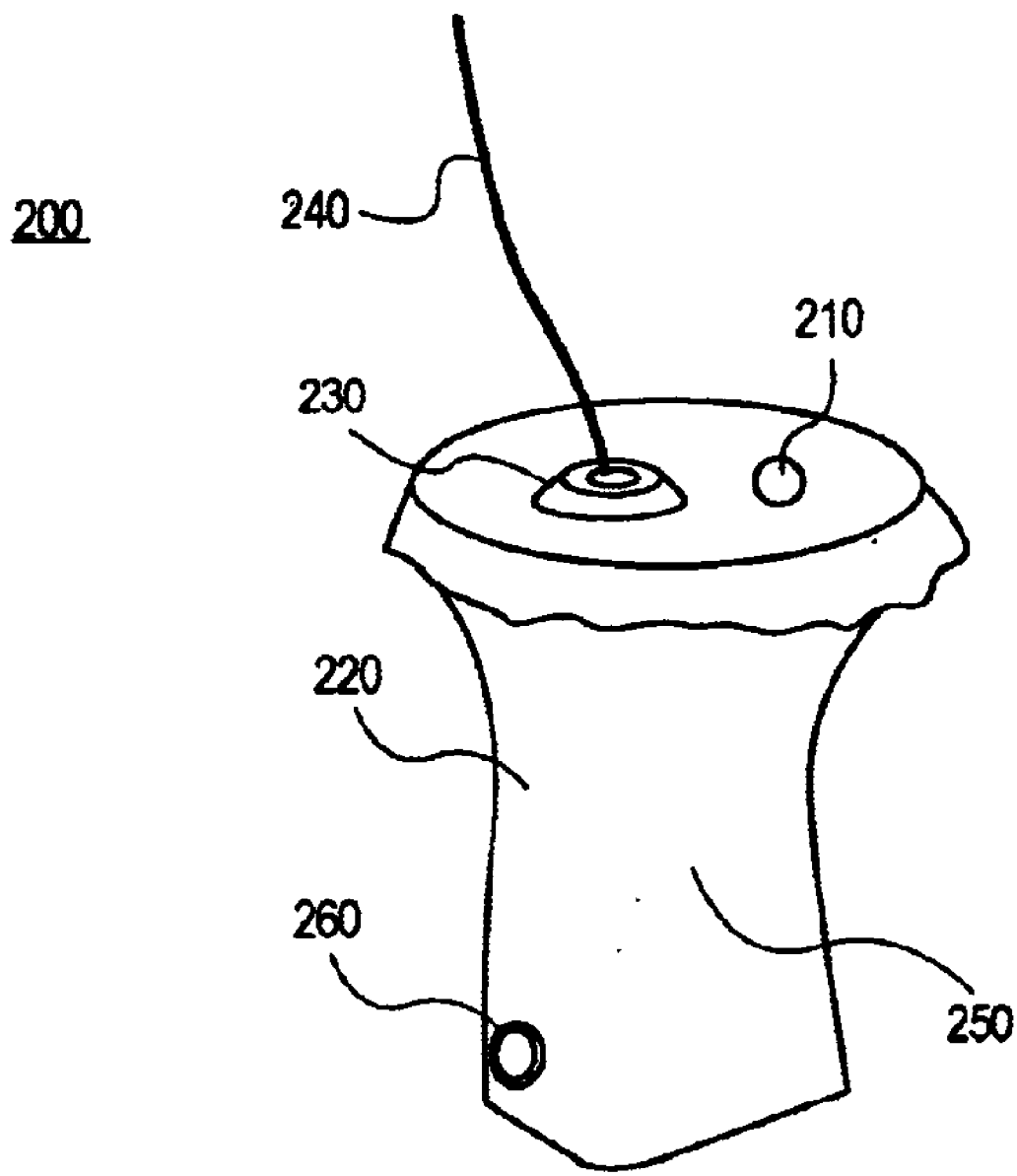
FIG. 2 illustrates an embodiment of a biohazard container appropriate for a single use.

FIG. 2 illustrates an embodiment of a biohazard container appropriate for a single use. In FIG. 2, biohazard container 200, first membrane 210, second membrane 220, inlet port 230, tube 240 and containment volume 250 are shown. Also shown is optional outlet port 260. The particular embodiment in FIG. 2 has a portion of the second membrane formed into a circular shape to fit with the lip of a rigid receptacle (not shown). Many other shapes are readily apparent to the skilled person.

In FIG. 2, first membrane 210 and second membrane 220 are coupled with inlet port 230 so as to enclose containment volume 250. Biohazardous fluids flow under the action of gravity from a surgical site (see FIG. 1) through the inlet port to the containment volume. Particular embodiments may be adapted for final disposal of the biohazardous fluid in another location by use of outlet port 260.

Container 200 includes first membrane 210. The first membrane allows the gas pressure within the containment volume to remain substantially constant as biohazardous fluid enters. The air displaced by the entering biohazardous fluid passes through the first membrane. However, biohazardous fluids, including aerosols, are not passed. They are filtered out.

As described, first membrane 210 is characterized by being permeable to gasses and impermeable to liquids and aerosols. In particular embodiments, the first membrane not only is impermeable to liquids, but also does not pass objects having a size greater than about 10 micrometers or greater than about 1 micrometer or greater than about 0.1 micrometer. These physical length scales are smaller than characteristic length scales of bacteria and viruses and thus block their passage out of the containment volume 250. Common term-of-art acronyms for filters with the above-described properties include but are not limited to HEPA (high efficiency particulate air) and ULPA (ultra low penetration air). Standards for the above-described filtering performance include but are not limited to DIN 2418B Ti-E EU 13 (Germany) and Standard 5415 (United Kingdom).

First membrane 210 may be fabricated from a polymer. One group of suitable materials consists of a genus of fluoropolymers, including the species polytetrafluoroethylene (PTFE) and polychlorotrifluoroethylene (PCTFE) contained in the genus. Many other materials will be apparent to a skilled person.

Suitable materials for first membrane 210 may be formed into a variety of structures, as is well known in the art of filtration. Suitable structures may be microporous, or granular or a network of interconnected particles. Moreover, catalytic substances may be provided on surfaces of the structure.

Preferably, embodiments of a first membrane or a second membrane are thin. Many embodiments comprise cloth-like structure. However, the first or the second membranes may be thick. Examples of suitable first membrane materials and structures are contained in U.S. Pat. Nos. 5,507,847, 5,496, 396, 5,462,586, 5,417,743, 4,983,434, 4,931,178, and 4,025, 679, all of which are hereby incorporated in their entirety by reference.

Container 200 also includes second membrane 220. The second membrane may be fabricated from a polymer or other material so as to be characterized by impermeability to gasses and liquids. Many appropriate materials are readily apparent to the skilled person. Preferably, the second membrane is thin. However, as discussed above, the second membrane may be thick. Further, the second membrane may be transparent or opaque to visible light. Materials that are transparent to visible light are preferred since they allow medical personnel to monitor the contents of the container for fill level, color, etc.

Figure 3A:
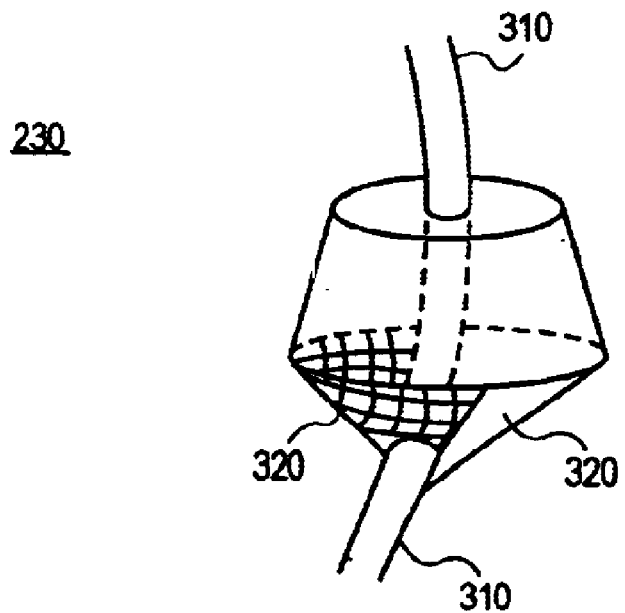
FIGS. 3A–3B illustrate a splash and spill sealed design for an inlet port embodiment.
Figure 3B:
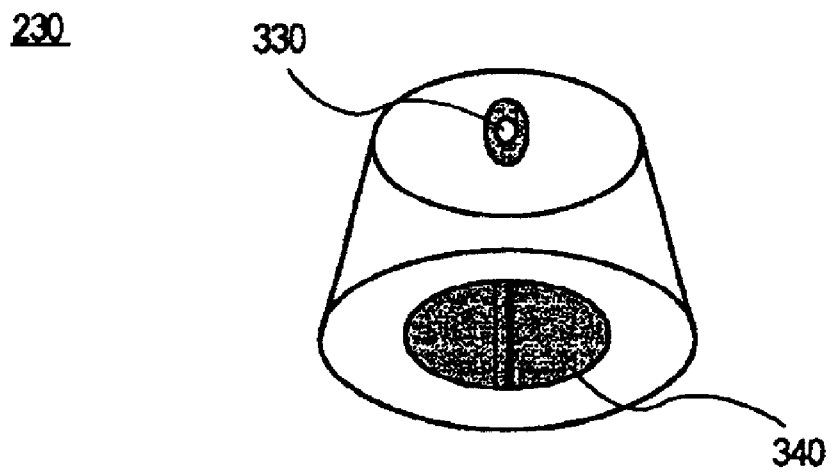

FIG. 3A and FIG. 3B show different embodiments of inlet port 230 (see FIG. 2) illustrating splash and spill sealed designs. In FIG. 3A, drain tube 310 and leaf 320 are shown. In FIG. 3B, diaphragms 330 and 340 are shown. For the embodiment shown in FIG. 3A, the drain tube is shown after insertion into the inlet port. Two leaves are shown in FIG. 3A, however, other embodiments have more than two leaves. The leaves may be fabricated with an elastic polymer or a silastic material to form an effective barrier against fluid splashing back, spilling or otherwise exiting through the inlet port. In FIG. 3B, diaphragm 330 is typically a single piece. In contrast, diaphragm 340 may be a single piece or may include a plurality of portions. Some of the portions may overlap. The overlapping portions may be semi-circular. Both diaphragm 330 and 340 may be fabricated from an elastic material, such as rubber or synthetic rubber or polymer. Silastic material is preferred since it self-seals about the surface of a member such as the drain tube that pierces the diaphragm membrane.

Figure 4A:
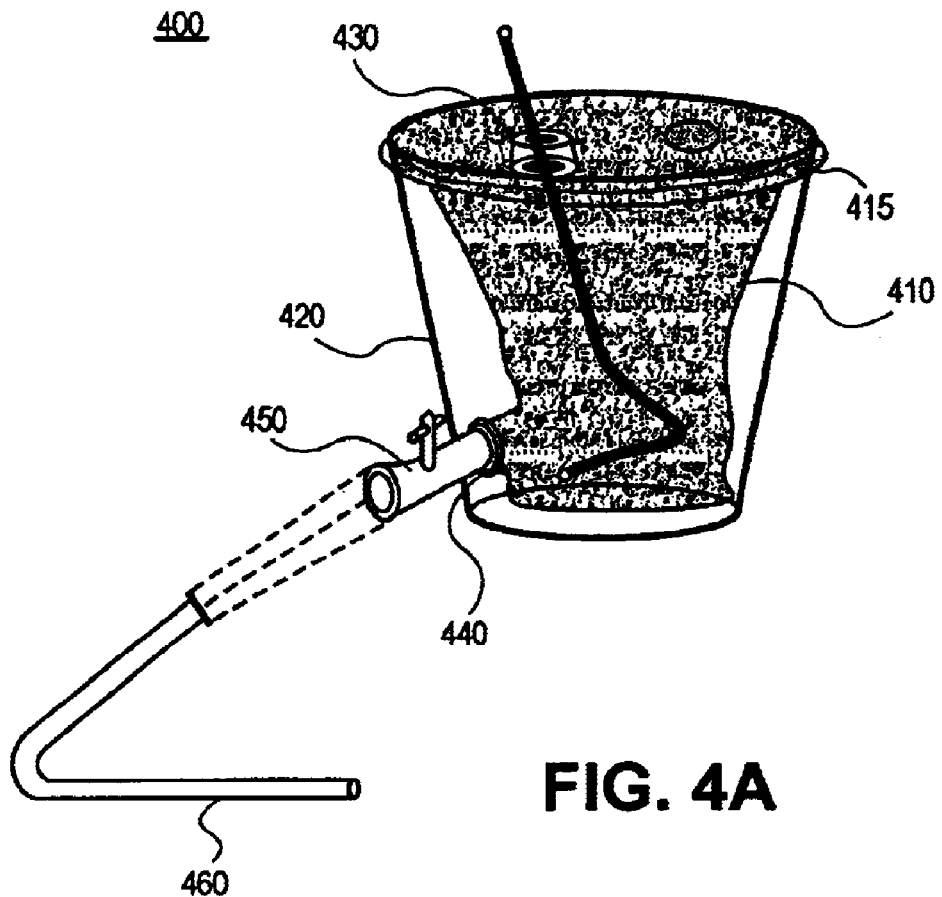
FIGS. 4A–4B illustrate an embodiment of the biohazard containment system.
Figure 4B:
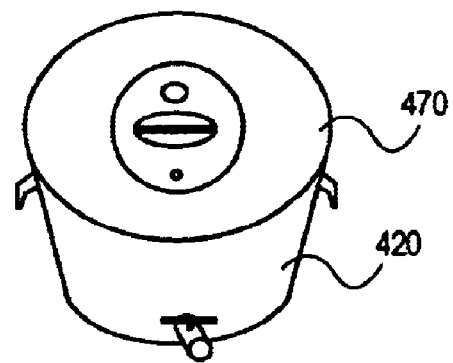

FIG. 4A and FIG. 4B illustrate an embodiment of the biohazard containment system. The system comprises both reusable and single-use elements. In FIG. 4A, containment system 400, single-use liner assembly 410, receptacle 420, inlet port 430, outlet port 440 and optional spigot 450, drainage tube 460 are shown. FIG. 4B shows lid 470 in a top view. According to the embodiment shown, the receptacle is typically reusable and is characterized by enclosing a portion of the liner assembly. The receptacle may transmit visible light so that, in combination with a see-through liner assembly, medical personnel can monitor the contents. Elastic band 415 secures the liner assembly 410 to receptacle 420.

Liner assembly 410 is typically single-use, meaning that the assembly may be disposed of without emptying it. In principal, particular embodiments of the liner assembly including an outlet port and a spigot coupled to the outlet port could be drained and reused. Preferred embodiments of the receptacle 420 are rigid and substantially enclose a single-use liner assembly, as exemplified in the embodiment shown in FIG. 4A. Particular embodiments include a lid 470 that may be secured to receptacle 420, as shown in FIG. 4B. An elastic band is preferably included in the liner assembly to secure the liner to the receptacle during use.

In practice, a typical embodiment of containment system 400 is connected to tubing that is in fluid communication with the surgery site. Biohazardous fluids from the surgery site flow under the action of gravity to the containment system. As the fluid is collected, air from within the system vents into the atmosphere to maintain a substantially constant pressure. The containment system prevents the escape of biohazards by the combination of impermeable membranes and seals about inlet tubing. When the system is full of fluid, the fluid may be disposed of complete with the liner assembly 410, or drained under controlled conditions through outlet port 440 and drainage tube 460. Preferably, the drainage tube is sufficiently long to allow the exit of the drainage tube to be placed far down a waste drain to minimize potential exposure of personnel to the drained biohazard.

The reusable and single-use elements described above combine to form an efficient and cost effective solution to mitigate risks posed by exposure to biohazardous fluids. As is readily apparent to a skilled person, the invention is not limited to the above-described embodiments. Rather, different configurations and embodiments can be developed without departing from the scope of the invention and are intended to be included within the scope of the claims set forth below.

What is claimed is:

1. A biohazard system, comprising:
   a container defining a substantially closed containment volume for biohazards, the container being impermeable to at least liquids;
   a first membrane coupled to the containment volume, the first membrane being permeable to at least gases, wherein the first membrane permits at least gases to move between the container and an outside of the container; and
   an elastic inlet coupled to the container, the elastic inlet receiving a tube, wherein the elastic inlet permits at least liquids to at least move into the container through the tube.

2. The biohazard container of claim 1, wherein the first membrane is impermeable to objects having a size greater than about 10 micrometers.

3. The biohazard container of claim 1, wherein the first membrane is impermeable to objects having a size greater than about 1 micrometer.

4. The biohazard container of claim 1, wherein the first membrane is impermeable to objects having a size greater than about 0.1 micrometer.

5. The biohazard container of claim 1, wherein the first membrane comprises a polymer material.

6. The biohazard container of claim 5, wherein the first membrane comprises a polymer material selected from a group consisting of the genus of fluoropolymers.

7. The biohazard container of claim 6, wherein the container is fabricated from a material that is transparent to visible light.

8. The biohazard container of claim 1, wherein the elastic inlet includes at least one diaphragm.

9. The biohazard container of claim 8, wherein the at least one diaphragm comprises a plurality of leaves.

10. The biohazard container of claim 8, wherein the at least one diaphragm comprises a plurality of overlapping semi-circular disk portions.

11. The biohazard container of claim 8, wherein at least a portion of the at least one diaphragm is fabricated from a silastic material.

12. A biohazard system, comprising:
   a container defining a substantially closed containment volume for biohazards, the container being impermeable to at least liquids;
   a first membrane coupled to the containment volume, the first membrane being permeable to at least gases, wherein the first membrane permits at least gases to move between the container and an outside of the container; and
   an elastic inlet coupled to the container, the elastic inlet comprises a plurality of leaves, at least one leaf of the plurality of leaves receiving a member pierced through the elastic inlet.

13. The biohazard container of claim 12, wherein the first membrane is impermeable to objects having a size greater than about 10 micrometers.

14. The biohazard container of claim 12, wherein the first membrane is impermeable to objects having a size greater than about 1 micrometer.

15. The biohazard container of claim 12, wherein the first membrane is impermeable to objects having a size greater than about 0.1 micrometer.

16. The biohazard container of claim 12, wherein the first membrane comprises a polymer material.

17. The biohazard container of claim 16, wherein the first membrane comprises a polymer material selected from a group consisting of the genus of fluoropolymers.

18. The biohazard container of claim 12, wherein the container is fabricated from a material that is transparent to visible light.

19. A biohazard containment system, comprising:
   a liner assembly comprising:
      a container defining a substantially closed containment volume operating at substantially atmospheric pressure for biohazards, the container being impermeable to at least liquids;
      a first membrane coupled to the containment volume, the first membrane being permeable to at least gases, wherein the first membrane permits at least gases to move between the container and an outside of the container;
      an elastic inlet coupled to the container, the elastic inlet receiving a tube; and
      an outlet coupled to the container; and
   a rigid receptacle for receiving the liner assembly, wherein the rigid receptacle forms an enclosure for at least a portion of the liner assembly.

20. The biohazard containment system of claim 19, wherein the liner assembly further comprises an elastic band.

21. The biohazard containment system of claim 19, wherein the liner assembly is transparent to visible light.

22. The biohazard containment system of claim 19, wherein the rigid reusable receptacle is transparent to visible light.

23. The biohazard containment system of claim 19, further comprising a lid that is securable to the rigid receptacle, the combination of the rigid receptacle and lid containing the liner assembly.

24. The biohazard containment system of claim 19, further comprising a drainage tube coupled to the outlet port and in fluid communication with the substantially closed containment volume enclosed by the liner assembly.

25. A biohazard containment system, comprising:
   a liner assembly comprising:
      a container defining a substantially closed containment volume for biohazards, the container being impermeable to at least liquids;
      a first membrane, the first membrane being permeable to at least gases at substantially atmospheric pressure during operation; and
      an elastic inlet coupled to the container, wherein the elastic inlet comprises a plurality of leaves, at least one leaf of the plurality of leaves receiving a member pierced through the elastic inlet; and
      an outlet coupled to the container, and
   a rigid receptacle for receiving the liner assembly, wherein the rigid receptacle forms an enclosure for at least a portion of the liner assembly.

26. The biohazard containment system of claim 25, wherein the liner assembly further comprises an elastic band.

27. The biohazard containment system of claim 25, wherein the liner assembly is transparent to visible light.

28. The biohazard containment system of claim 25, wherein the rigid receptacle is transparent to visible light.

29. The biohazard containment system of claim 25, further comprising a lid that is securable to the rigid receptacle, the combination of the rigid receptacle and lid containing the liner assembly.

30. The biohazard containment system of claim 25, further comprising a drainage tube coupled to the outlet port and in fluid communication with the substantially closed containment volume enclosed by the liner assembly.

31. A method for containing biohazardous fluids, comprising:

transferring a biohazardous liquid to a containment volume via an elastic inlet receiving a tube by action of gravity at substantially atmospheric pressure on the biohazardous liquid; and maintaining a substantially constant gas pressure in the containment volume during the transfer.

32. The method of claim 31, wherein maintaining a substantially constant gas pressure in the containment volume comprises:

releasing gas from the containment volume.

* * * * *